United States Patent [19]
Imai et al.

[11] Patent Number: 5,476,968
[45] Date of Patent: Dec. 19, 1995

[54] N,N'-BIS(P-HYDROXYMETHYLPHENYL)-BENZIDINE COMPOUNDS AND METHOD FOR PREPARING THE SAME

[75] Inventors: Akira Imai; Katsumi Nukada, both of Minamiashigara, Japan

[73] Assignee: Fuji Xerox Co., Ltd., Tokyo, Japan

[21] Appl. No.: 293,924

[22] Filed: Aug. 22, 1994

[30] Foreign Application Priority Data

Aug. 23, 1993 [JP] Japan .................................. 5-227868

[51] Int. Cl.⁶ .................... C07C 223/06; C07C 211/54; C07C 211/56
[52] U.S. Cl. .................... 564/309; 564/307; 568/453; 568/768
[58] Field of Search ................................. 564/309, 307; 568/453, 768

[56] References Cited

U.S. PATENT DOCUMENTS

| | | | |
|---|---|---|---|
| 2,576,311 | 11/1951 | Schlesinger et al. | 568/764 X |
| 2,683,721 | 7/1954 | Schlesinger et al. | 568/764 X |
| 3,085,003 | 4/1963 | Morris | 568/764 X |
| 4,047,948 | 9/1977 | Horgan | 430/54 |
| 4,299,897 | 11/1981 | Stolka et al. | 430/59 |
| 4,556,740 | 12/1985 | Hansen et al. | 568/13 |
| 4,588,666 | 5/1986 | Stolka et al. | 430/59 |
| 4,764,625 | 8/1988 | Turner et al. | 548/442 |
| 4,801,517 | 1/1989 | Frechet et al. | 430/59 |
| 4,871,634 | 10/1989 | Limburg et al. | 430/54 |
| 4,933,245 | 6/1990 | Akasaki et al. | 430/59 |
| 5,245,030 | 9/1993 | Fukui et al. | 540/596 |
| 5,252,750 | 10/1993 | Hashimoto et al. | 549/59 |
| 5,298,661 | 3/1994 | Shimada et al. | 564/307 |
| 5,344,985 | 9/1994 | Tanaka et al. | 564/426 |

FOREIGN PATENT DOCUMENTS

| | | | |
|---|---|---|---|
| 61-132954 | 6/1986 | Japan | 430/59 |
| 4-300854 | 10/1992 | Japan | 564/307 |

*Primary Examiner*—Floyd D. Higel
*Attorney, Agent, or Firm*—Oliff & Berridge

[57] ABSTRACT

A N,N'-bis(p-hydroxymethylphenyl)benzidine compound having the following formula (I):

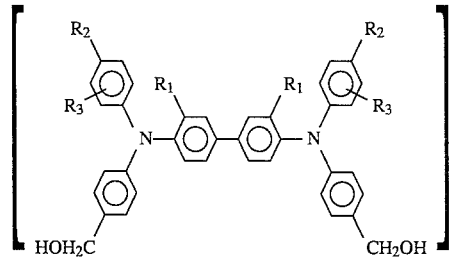

(I)

wherein $R_1$ represents a hydrogen atom, a methyl group or a methoxy group; $R_2$ represents an alkyl group having one to four carbon atoms, a methoxy group or an ethoxy group; and $R_3$ represents a hydrogen atom or a methyl group, is intended to be used as a charge transporting material of an electrophotographic photoreceptor. A method for preparing the compound includes formylating a N,N'-diphenylbenzidine derivative having the following formula (II):

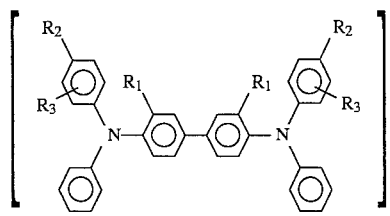

(II)

by the conventional Viismeier reaction to obtain a N,N'-bis(p-formylphenyl) benzidine derivative of the following formula (III):

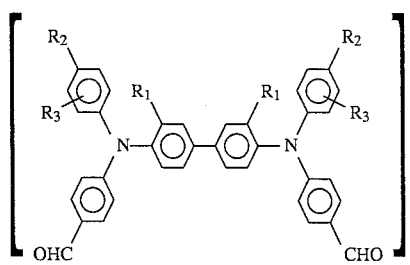

(III)

and reducing the derivative with a boron hydride salt or an aluminum hydride salt.

7 Claims, 8 Drawing Sheets

N,N'-BIS(P-HYDROXYMETHYLPHENYL)BENZIDINE COMPOUNDS AND METHOD FOR PREPARING THE SAME

FIELD OF THE INVENTION

The present invention relates to a novel benzidine derivative, in particular to a N,N'-bis(p-hydroxymethylphenyl)benzidine derivative useful as a charge transporting material of an electrophotographic photoreceptor or as an intermediate thereof.

BACKGROUND OF THE INVENTION

Inorganic photoconductive materials such as selenium, cadmium sulfide and zinc oxide have been conventionally used as electrophotographic light sensitive materials. Recently, many suggestions that organic photoconductive materials can be used as electrophotographic photoreceptors have been made. In particular, research and development on a function separated type photoreceptor in which functions of light carrier generation and transportation are divided into separate materials, i.e., charge generating materials and charge transporting materials, has recently gained popularity and has already been used practically. The use of charge transporting material such as, various hydrazones, stilbenes and triphenylamine derivatives have been proposed. In addition, benzidine derivatives useful as charge transporting materials have been described, e.g., in JP-A-61-132954 (The term "JP-A" as used herein means as "unexamined, published Japanese patent application").

Although, these organic photoconductive materials have advantages such as low manufacturing costs, good safety and high production rate, they are still inferior to inorganic photoconductive materials with respect to light response rate, stability, mechanical durability or the like. Thus, materials having better characteristics have been desired.

SUMMARY OF THE INVENTION

The object of the present invention is to provide a novel N,N'-bis(p-hydroxymethylphenyl)benzidlne derivative that is useful as a charge transporting material in an electrophotographic photoreceptor or as an intermediate thereof.

As a result of earnest investigations, the present inventors have found that N,N,'-diphenylbenzidine derivatives in which methylol group is introduced show better physical characteristics among benzidine compounds.

Accordingly, the present invention provides a novel N,N,'-bis(p-hydroxymethylphenyl)benzidine derivative of the following formula (I):

general formula (I)

wherein $R_1$ represents a hydrogen atom, a methyl group or a methoxy group; $R_2$ represents an alkyl group having one to four carbon atoms, a methoxy group or an ethoxy group; $R_3$ represents a hydrogen atom or a methyl group.

The N,N'-bis(p-hydroxymethylphenyl)benzidine derivative of the present invention may be prepared by formylating an N,N'-diphenylbenzidine derivative having the following general formula (II) by a known method into a N,N'-bis(p-formylphenyl)benzidine derivative, and reducing the derivative.

general formula (II)

general formula (III)

wherein $R_1$, $R_2$ and $R_3$ are as defined above.

DETAILED DESCRIPTION OF THE INVENTION

The present invention will be detailed hereinafter.

The formylating reaction of the N,N'-diphenyl benzidine derivative having the above formula (II) may be carried out using a formylating agent, in which a substituted formamide and an acid chloride are combined, in a conventional Wilsmeler reaction. In particular, a combination of N,N-dimethylformamide and phosphorus oxychloride is most preferable in a laboratory preparation, and a combination of N,N-dimethylformamide and phosgene is most preferable in an industrial preparation.

The reducing reaction of the N,N'-bis(p-formylphenyl)benzidine derivative having the above general formula (III) and obtained by the formylating reaction may be carried out using reducing agents which can convert a carbonyl group into a methylene group, such as boron hydride salt or aluminum hydride salt. When a proton solvent such as alcohol is selected as a reaction solvent, sodium boron hydride is most preferable as a reducing agent, and when a non-proton solvent such as ether is selected, lithium aluminum hydride is used most preferably as reducing agent.

The N,N'-bis(p-hydroxymethylphenyl)benzidine derivative having the above general formula (I) thus obtained may include the following compounds (1) to (8).

In addition, the N,N'-bis(p-hydroxymethylphenyl)benzidine derivatives shown in the following Table 1 may be obtained.

TABLE 1

| Compound | $R_1$ | $R_2$ | $R_3$ |
|---|---|---|---|
| 9 | $CH_3$ | $OC_2H_5$ | H |
| 10 | H | $CH_3$ | H |
| 11 | H | $C_2H_5$ | H |
| 12 | H | i-$C_3H_7$ | H |
| 13 | H | t-$C_4H_9$ | H |
| 14 | H | $OCH_3$ | H |
| 15 | H | $OC_2H_5$ | H |
| 16 | H | $CH_3$ | 3-$CH_3$ |
| 17 | H | $C_2H_5$ | 3-$CH_3$ |
| 18 | H | i-$C_3H_7$ | 3-$CH_3$ |
| 19 | H | t-$C_4H_9$ | 2-$CH_3$ |
| 20 | H | $OCH_3$ | 3-$CH_3$ |
| 21 | H | $OC_2H_5$ | 2-$CH_3$ |

The following examples are provided to further illustrate and explain the present invention, and it is intended that the scope of the present invention not be limited to the specific examples thus provided.

EXAMPLE 1

25 ml (0.1 mol) of N,N-dimethylformamide was added into a solution of 55 g (0.1 mol) of N,N'-diphenyl-N,N'-bis(p-tolyl)- 3,3'-dimethyl benzidine in 200 ml of methylene chloride, and 23 ml of phosphorus oxychloride was added dropwise into the mixture at 5° C. under ice-cooling. The mixture was then stirred for one hour, heated under reflux at 40° C. for two hours, left to cool, diluted with 500 ml of methylene chloride, and neutralized with an aqueous solution of potassium bicarbonate. The organic phase of the neutralized solution was separated and absolute sodium sulfate was added. The mixture was then dried and concentrated under reduced pressure and the residue obtained was purified by column chromatography [silica gel;methylene chloride/hexane (1/2)] to give 34 g of the following formylated compound (1'). Yield 56%. Melting point 152° to 155° C. Green yellow crystals.

Figure 1:
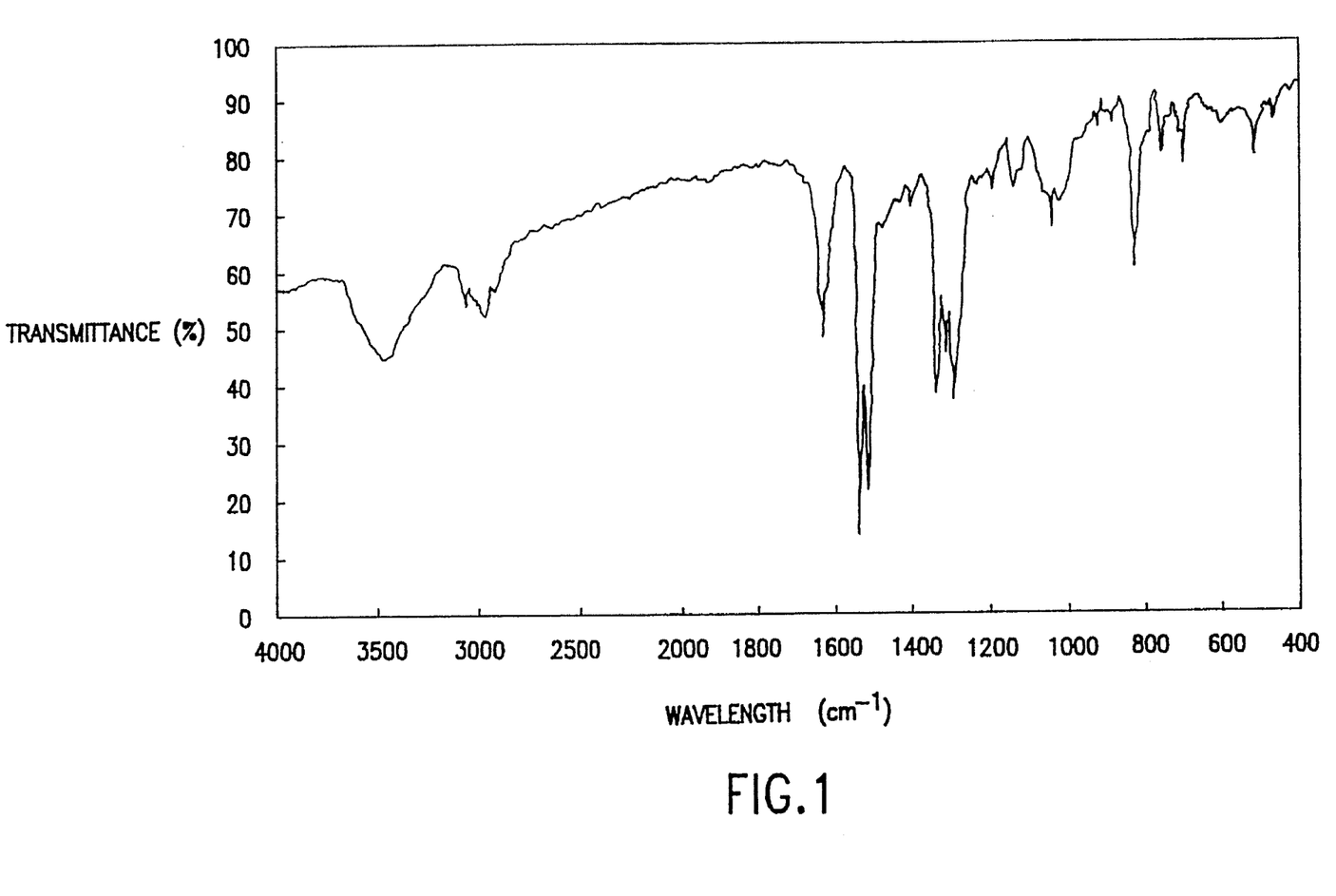
FIG. 1 is an infrared absorption spectrum of the Compound (1') obtained as a synthetic intermediate in Example 1.
Figure 2:
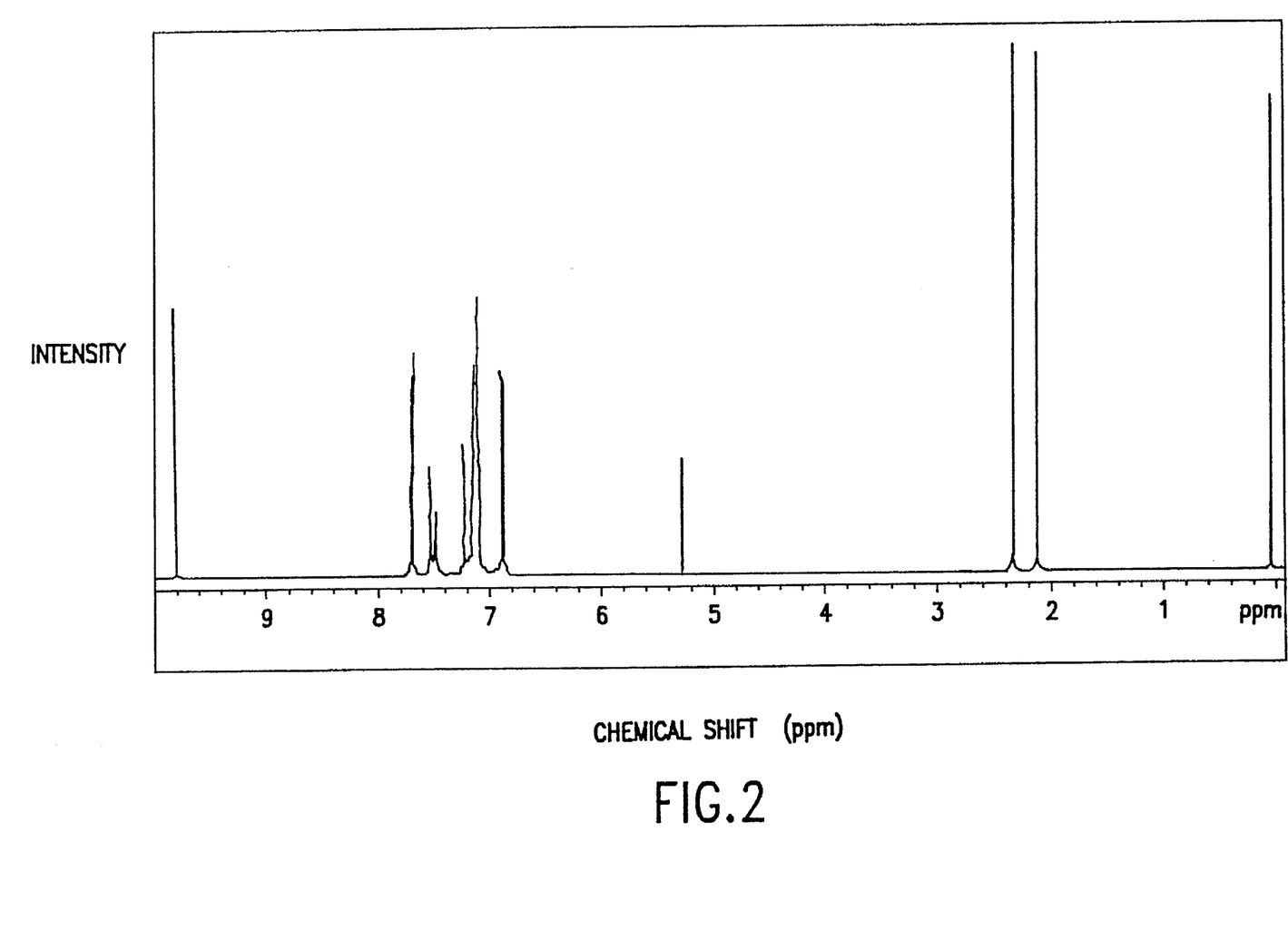
FIG. 2 is a NMR spectrum of the Compound (1') obtained as a synthetic intermediate in Example 1.

Infrared absorption spectrum (KBr tablet method) and NMR spectrum ($^1$H; in CDCl$_3$ solvent) of the compound (1') obtained are shown in FIGS. 1 and 2.

30 g (0.05 mol) of compound (1') was then dispersed in 250 ml of ethanol., 1.0 g (0.026 mol) of sodium boron hydride was added to the mixture and the mixture was stirred at 70° C. for one hour. After cooling, 100 ml of water was added to the mixture and the resulting white precipitate was filtered off and recrystallized from 1.5l of methanol to give 22.8 g of the above compound (1). Yield 784. Melting point 113° to 116° C. Colorless crystals.

Figure 3:
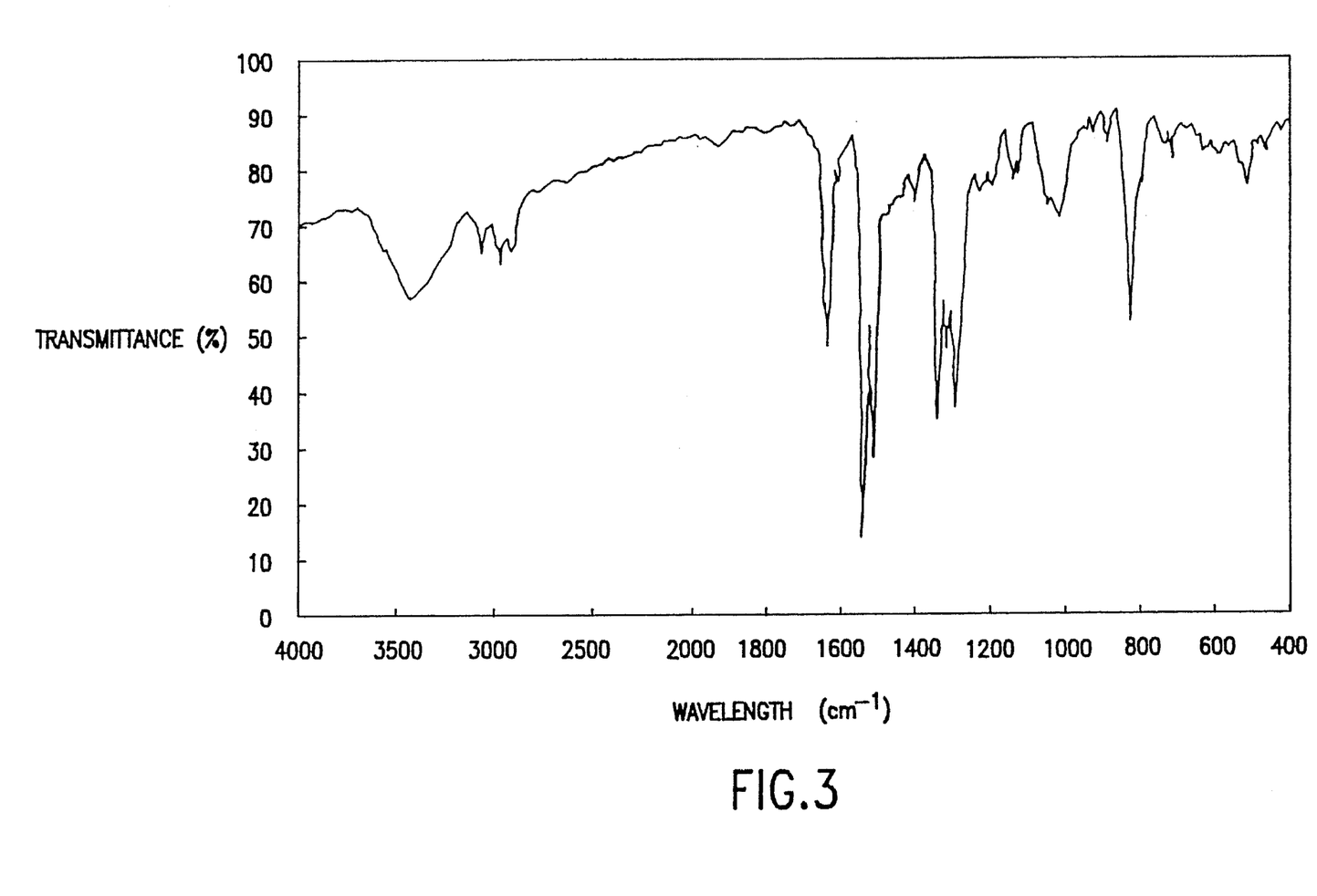
FIG. 3 is an infrared absorption spectrum of the Compound (1) prepared in Example 1.
Figure 4:
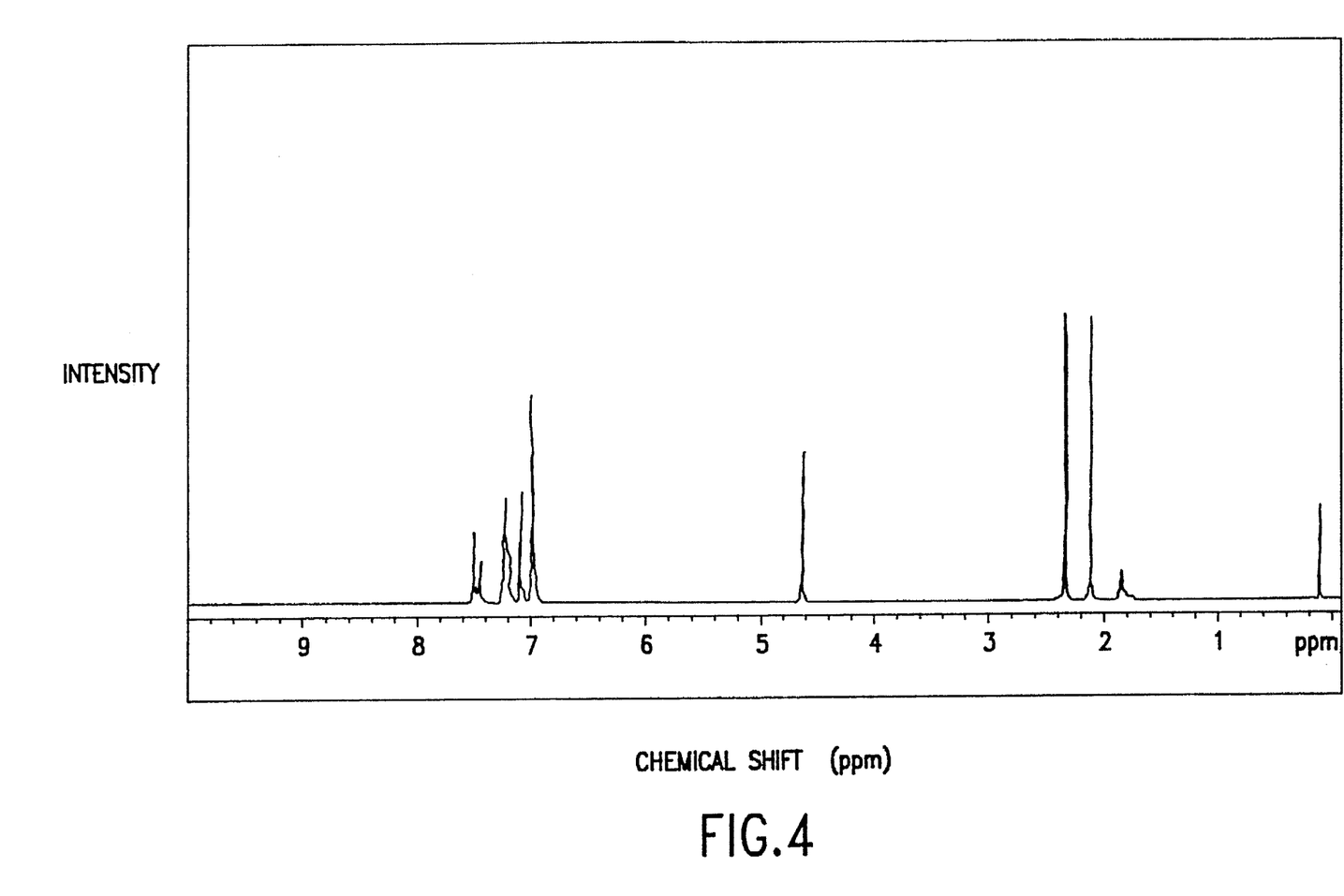
FIG. 4 is a NMR spectrum of the Compound (1) prepared in Example 1.

Infrared absorption spectrum (KBr tablet method) and NMR spectrum ($^1$H; in CDCl$_3$ solvent) of the compound (1) obtained are shown in FIGS. 3 and 4.

EXAMPLE 2

31 ml of N,N-dimethylformamide was added a solution of 54.5 g (0.1 mol) of N,N'-diphenyl-N,N'-bis(p-ethylphenyl-)benzidlne in 250 ml of methylene chloride, and 20 ml of phosphorus oxychloride was added dropwise into the mixture at 5° C. under ice-cooling. The mixture was then stirred for two hours, heated under reflux at 40° C., left to cool, diluted with 200 ml of methylene chloride, and neutralized with an aqueous solution of potassium carbonate. The organic phase of the neutralized solution was separated and absolute sodium sulfate was added. The mixture was then dried and concentrated under reduced pressure and the residue obtained was purified by column chromatography to give 39.4 g of the following formylated compound (11'). Yield 66%. Melting point 190° to 193° C. Yellow crystals.

Figure 5:
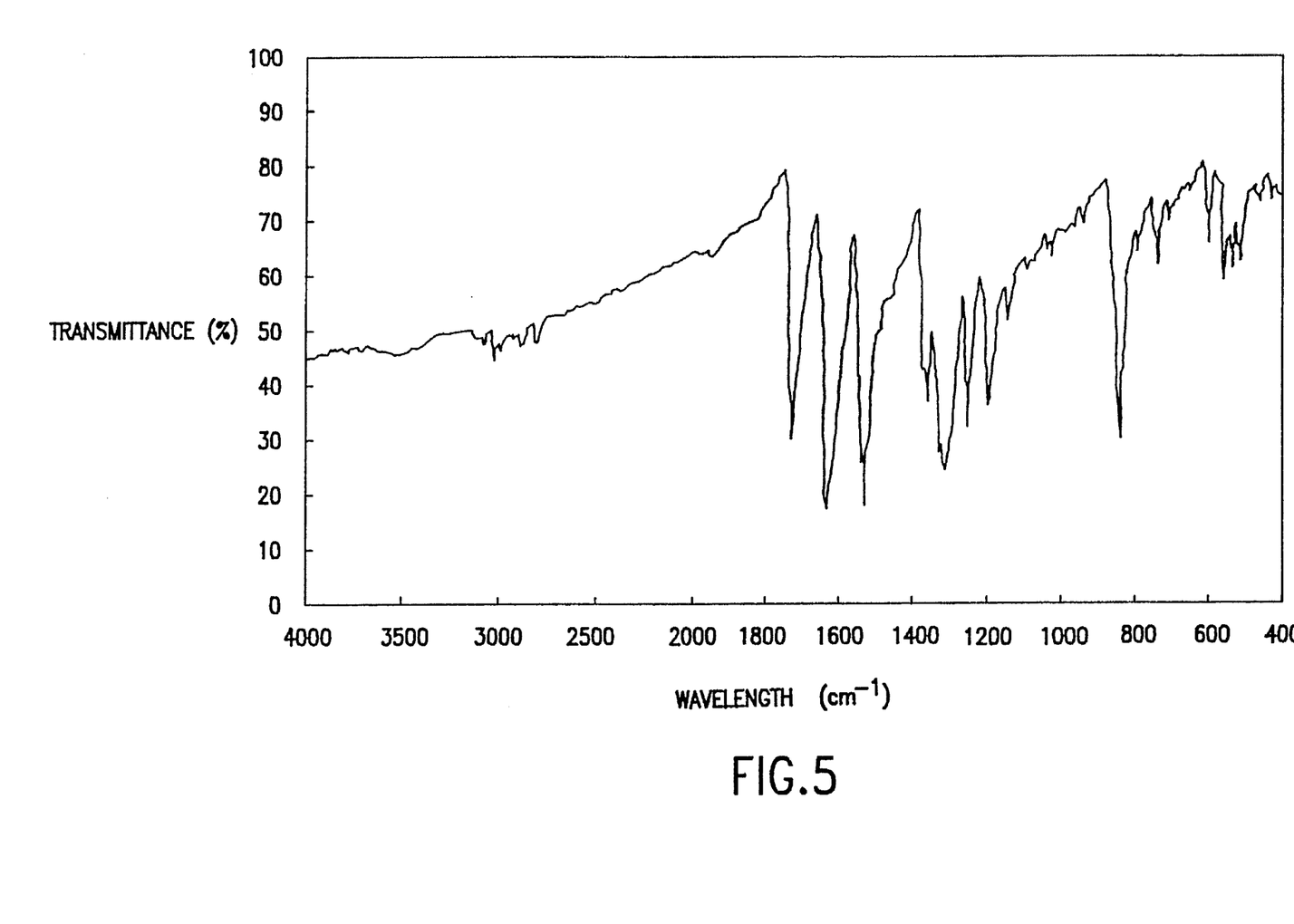
FIG. 5 is an infrared absorption spectrum of the Compound (11') obtained as a synthetic intermediate in Example 2.
Figure 6:
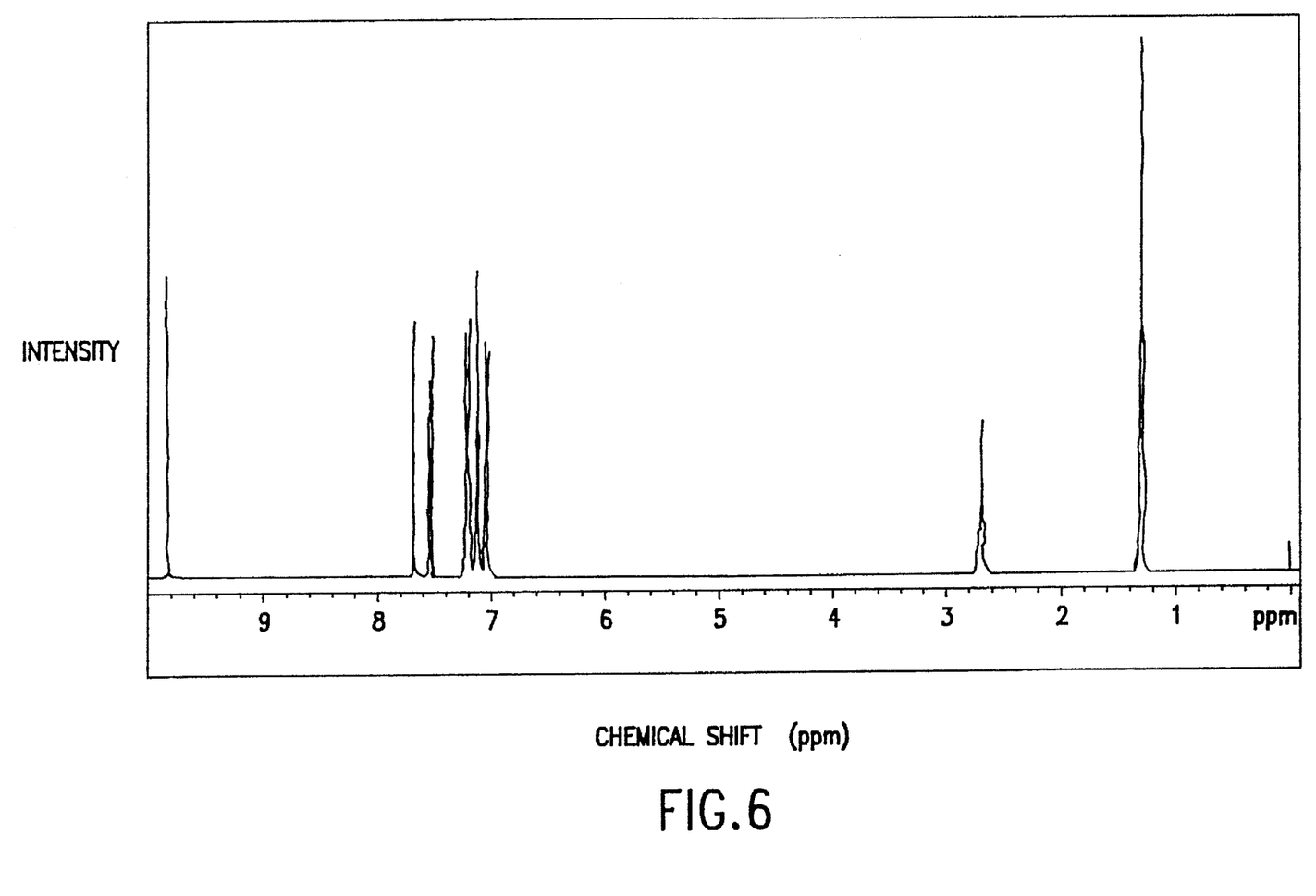
FIG. 6 is a NMR spectrum of the Compound (11') obtained as a synthetic intermediate in Example 2.

Infrared absorption spectrum (KBr tablet method) and NMR spectrum ($^1$H; in CDCl$_3$ solvent) of the compound (11') obtained are shown in FIGS. 5 and 6.

18.6 g (0.03 mol) of compound (11') was then dispersed in 200 ml of ethanol: 0.65 g (0.017 mol) of sodium boron hydride was added to the mixture and the mixture was stirred at 70° C. for one hour. After cooling, the mixture was diluted with 300 ml of water and the resulting white precipitate was filtered off. After drying, the mixture was purified by column chromatography (silica gel; toluene to ethanol) to give 13.3 g of the above compound (11). Yield 71%.

Figure 7:
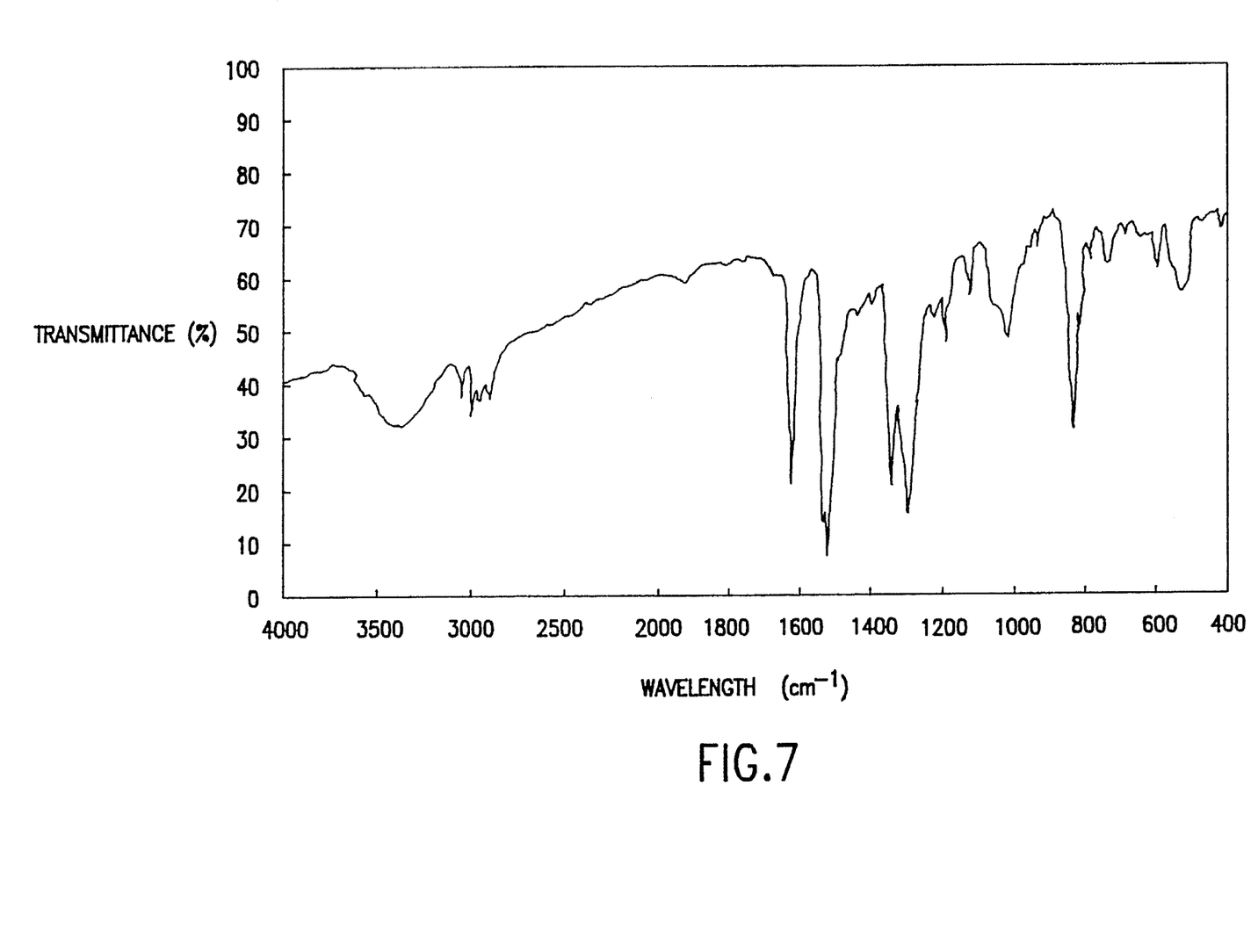
FIG. 7 is an infrared absorption spectrum of the Compound (11) prepared in Example 2.
Figure 8:
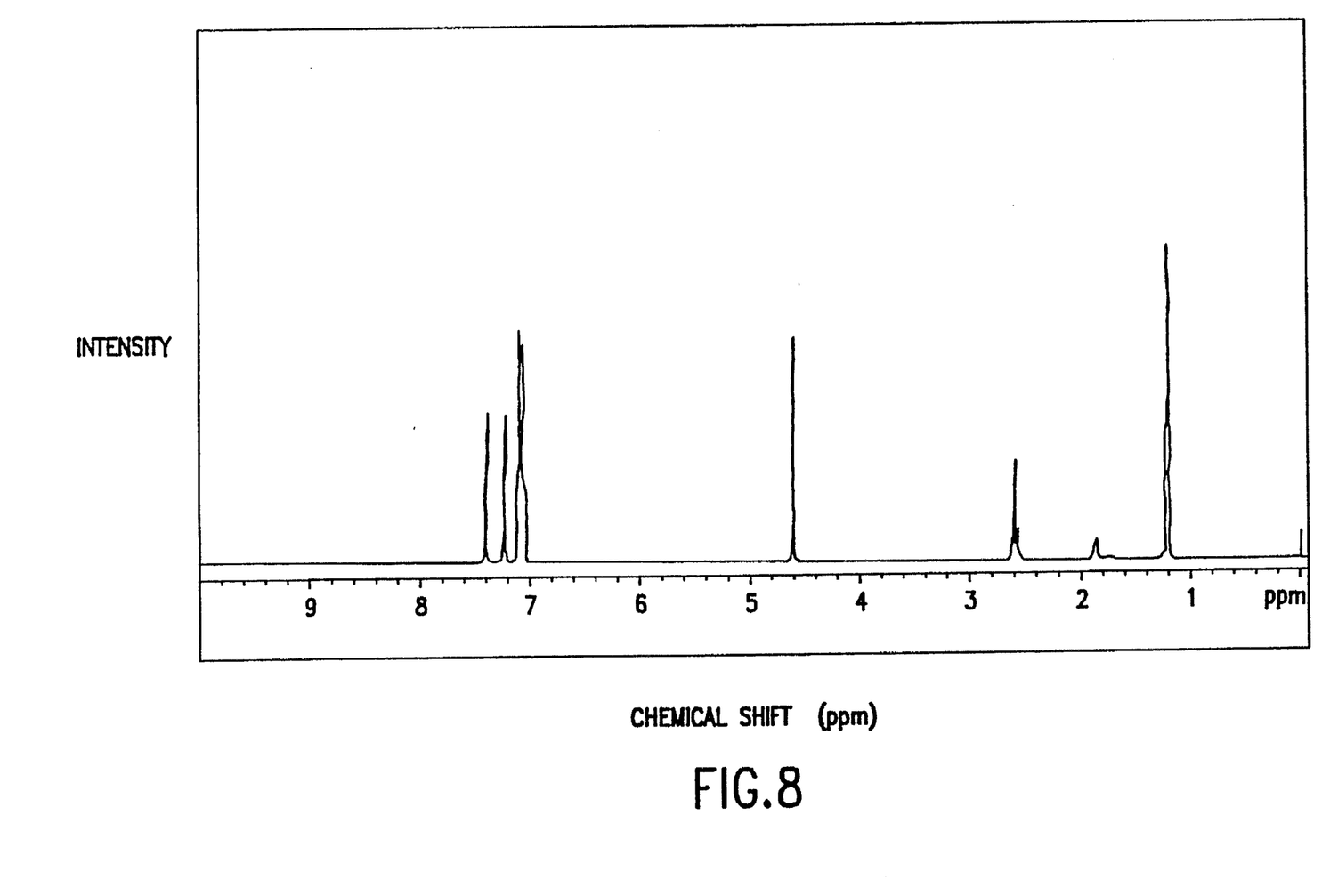
FIG. 8 is a NMR spectrum of the Compound (11) prepared in Example 2.

Infrared absorption spectrum (KBr tablet method) and NMR spectrum ($^1$H; in CDCl$_3$ solvent) of the compound (11) obtained are shown in FIGS. 7 and 8.

The novel N,N'-bis(p-hydroxymethylphenyl)benzidine derivative of the present invention is not only useful as a charge transporting material of an electrophotographic photoreceptor but also useful as an intermediate for the synthesis of various benzidine derivatives containing other electrophotographic materials utilizing the reactivity of the hydroxy group in the molecule.

While the invention has been described in detail and with reference to specific embodiments thereof, it will be apparent to one skilled in the art that various changes and modifications can be made therein without departing from the spirit and scope thereof.

What is claimed is:

1. An N,N,-bis(p-hydroxymethylphenyl) benzidine compound of the following formula (I), wherein $R_1$ represents hydrogen, methyl or methoxy; $R_2$ represents an alkyl substituent having one to four carbons, methoxy or ethoxy; and $R_3$ represents hydrogen or methyl.

2. A method for preparing the N,N'-bis(p-hydroxymethylphenyl)benzidine compound of the formula (I) as claimed in claim 1, wherein said method comprises:

reacting an N,N'-diphenylbenzidine compound of the following formula (II) with an amide and an acid halide to add formyl at the para position of each of the unsubstituted phenyl substitutents of the compound of formula (II) to obtain an N,N' -bis(p-formylphenyl-)benzidine compound of the following formula (III); and reducing said formyl substituents with a boron hydride salt or an aluminum hydride salt, wherein $R_1$ represents hydrogen, methyl or methoxy; $R_2$ represents an alkyl substitutent having one to four carbon atoms, methoxy or ethoxy; and $R_3$ represents hydrogen or methyl.

3. The method of claim 2, wherein said amide is a substituted formamide and said acid halide is an acid chloride.

4. The method of claim 3, wherein said substituted formamide is N,N-dimethylformamide and said acid chloride is phosphorous oxychloride.

5. The method of claim 3, wherein said substituted formamide is N,N-dimethylformamide and said acid chloride is phosgene.

6. The method of claim 2, wherein said boron hydride salt is sodium boron hydride.

7. The method of claim 2, wherein said aluminum hydride salt is lithium aluminum hydride.

* * * * *